(12) United States Patent
Carlsen et al.

(10) Patent No.: US 6,609,520 B1
(45) Date of Patent: Aug. 26, 2003

(54) CLOSED SUCTION CATHETER ADAPTOR AND ASSEMBLY CONTAINING THE SAME

(75) Inventors: Wayne D. Carlsen, West Jordan, UT (US); Chet M. Crump, Draper, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/702,375

(22) Filed: Oct. 31, 2000

(51) Int. Cl.⁷ .............................................. A61M 16/00
(52) U.S. Cl. ............................ 128/207.14; 128/205.19
(58) Field of Search ....................... 128/207.14–207.16, 128/200.26, 911, 912, DIG. 26, 205.12, 205.19, 909; 604/35, 171

(56) References Cited

U.S. PATENT DOCUMENTS

| | | | |
|---|---|---|---|
| 3,991,762 A | | 11/1976 | Radford |
| 4,270,778 A | | 6/1981 | Brownell |
| 4,569,344 A | | 2/1986 | Palmer |
| 4,641,646 A | | 2/1987 | Schultz et al. |
| 5,060,646 A | | 10/1991 | Page |
| 5,255,676 A | * | 10/1993 | Russo ................... 128/205.24 |
| 5,325,851 A | * | 7/1994 | Reynolds et al. ....... 128/207.14 |
| 5,349,950 A | * | 9/1994 | Ulrich et al. ........... 128/207.14 |
| 5,354,267 A | * | 10/1994 | Niermann et al. ...... 128/207.14 |
| 5,355,876 A | * | 10/1994 | Brodsky et al. ........ 128/202.27 |
| 5,368,017 A | * | 11/1994 | Sorenson et al. ....... 128/200.26 |
| 5,390,669 A | | 2/1995 | Stuart et al. |
| 5,398,679 A | | 3/1995 | Freed |
| 5,460,613 A | * | 10/1995 | Ulrich et al. ........... 128/207.14 |
| 5,490,503 A | * | 2/1996 | Hollister ................ 128/200.26 |
| 5,513,628 A | * | 5/1996 | Coles et al. ............ 128/200.26 |
| 5,582,161 A | * | 12/1996 | Kee ...................... 128/200.26 |
| 5,598,840 A | * | 2/1997 | Lund et al. ............ 128/202.27 |
| 5,611,336 A | * | 3/1997 | Page et al. ............. 128/200.26 |
| 5,687,714 A | | 11/1997 | Kolobow et al. |
| 5,720,282 A | * | 2/1998 | Wright ................. 128/203.12 |
| 5,735,271 A | * | 4/1998 | Lorenzen et al. ...... 1298/200.26 |
| 5,775,325 A | * | 7/1998 | Russo ................... 128/202.27 |
| 5,779,687 A | * | 7/1998 | Bell et al. .............. 128/207.16 |
| 5,919,174 A | * | 7/1999 | Hanson .................... 604/533 |
| 6,026,810 A | | 2/2000 | Baird |
| 6,227,200 B1 | * | 5/2001 | Crump et al. .......... 128/207.16 |

FOREIGN PATENT DOCUMENTS

| | | |
|---|---|---|
| DE | 2939794 A1 | 4/1981 |
| EP | 0347026 A2 | 12/1989 |
| WO | 9721386 | 6/1997 |
| WO | WO 9805371 | 10/1997 |
| WO | 0013730 | 3/2000 |
| WO | 0249680 A2 | 6/2002 |
| WO | WO 0249680 | 6/2002 |

OTHER PUBLICATIONS

U.S. patent application No. 09/702,376, filed Oct. 31, 2000.
International Search Report mailed Dec. 4, 2002.
EPO Search Report, Sep. 25, 2002.

* cited by examiner

*Primary Examiner*—Aaron J. Lewis
*Assistant Examiner*—Teena Mitchell
(74) *Attorney, Agent, or Firm*—Dority & Manning, P.A.

(57) ABSTRACT

An adaptor is used to connect a closed suction catheter assembly to an artificial airway, such as a tracheostomy tube. The adaptor includes a housing, the internal chamber of which includes structure to allow a patient to breathe through the adaptor when attached to artificial airway. The adaptor may further contain a release assembly for separating the housing of the adaptor from the tracheostomy tube.

26 Claims, 12 Drawing Sheets

CLOSED SUCTION CATHETER ADAPTOR AND ASSEMBLY CONTAINING THE SAME

FIELD OF THE INVENTION

The present invention relates generally to closed suction catheter assemblies used in respiratory applications.

BACKGROUND OF THE INVENTION

There are a number of different circumstances in which it is necessary for a person to have an artificial airway, such as a tracheostomy tube, placed in his or her respiratory tract. As used herein, the phrase "artificial airway" includes devices such as tracheostomy tubes, endotracheal tubes, and the like. Artificial airways keep the patient's natural airway open so that adequate lung ventilation can be maintained.

In certain situations, the artificial airway must be left in the patient for a prolonged period of time. For example, many persons suffering severe neck or head trauma use a tracheostomy tube in conjunction with mechanical ventilation during extended recovery and rehabilitation periods. In other situations, patients may require an artificial airway for an extended period of time without mechanical ventilation. In these situations, it is critical that respiratory secretions be periodically removed. This is typically accomplished by the use of a respiratory suction catheter that is advanced into and through the tracheostomy tube. As the suction catheter is withdrawn, a negative pressure (or vacuum) is applied to draw mucus and other secretions from the patient's airways and the interior of the artificial airway. While a substantial amount of the mucus and other secretions will be withdrawn through the lumen of the suction catheter, a portion of the mucus and other secretions will remain as a film on the outside of the catheter.

Patient secretions can contain infectious agents, such as streptococcus, pseudomonas, staphylococcus, and even HIV. It is, therefore, important to shield the clinician from contact with the catheter. Using an uncovered catheter, or "open" catheter, thus poses health risks to the clinician. When the catheter is withdrawn from the tracheostomy tube, the exterior of the catheter may be coated with patient secretions and it is often necessary to repeat the procedure two or three times. With each advancement and retraction of the catheter, the clinician has to be concerned with not only suctioning the patient, but also with avoiding contact with the potentially infectious agents on the exterior of the catheter. In addition, the clinician must be concerned with preventing the catheter from being accidentally contaminated with microbes from the surrounding area, for example the patient's gown, bed clothing, and other surrounding items which may transmit microbes. It is, therefore, equally as important to shield the patient from communicable pathogens in the environment and those that may be carried by the clinician.

A problem also arises with repeated attachment and detachment of the catheter assembly to a tracheostomy tube since the constant application of force against the tracheostomy tube causes irritation and discomfort to the patient. Another problem posed with repeated attachment and detachment of the catheter assembly is that two hands are generally required. One hand stabilizes the tracheostomy tube while the other pushes the distal end of the catheter assembly onto the tracheostomy tube or pulls the distal end away from the tracheostomy tube. (As used herein, "distal" refers to the direction of the patient and "proximal" refers to the direction of the clinician.)

In a closed suction catheter assembly, as set forth in U.S. Pat. Nos. 3,991,762 and 4,569,344, the catheter may be enveloped by a protective sleeve and include a valve mechanism disposed near the vacuum source. These features reduce the risk of contamination to both the patient and the care giver. At its distal end, the closed suction catheter may be attached to an artificial airway via one of a variety of connectors, including, for example, a multi-legged tracheostomy connector. One of the legs of the tracheostomy connector may be connected to a tracheostomy tube located within an aperture formed in the throat of the patient. When it is desired to remove secretions or mucus from the patient, the catheter is advanced through the connector and into the tracheostomy tube. Negative pressure is then applied to the other end of the catheter and secretions within the patient's respiratory system are evacuated. With the use of the closed suction catheter assembly, the ventilating circuit need not be detached from the patient during suctioning, and a single catheter may be used for an extended period, typically a 24-hour period.

Thus, there is a need for an adaptor for attachment of a closed suction catheter assembly to a tracheostomy tube or other artificial airway that effectively addresses at least some of the problems noted with conventional closed suction catheter assemblies.

SUMMARY OF THE INVENTION

Objects and advantages of the invention will be set forth in part in the following description, or may be obvious from the description, or may be learned through practice of the invention.

The present invention is directed to an adaptor for use with a closed suction catheter assembly for attachment to an artificial airway, such as a tracheostomy tube. It should be appreciated that the adaptor of the present invention may be described herein with reference to a "tracheostomy tube" in particular. This is for illustrative purposes only and it should be understood that the adaptor may be utilized with any configuration of an artificial airway.

The adaptor is configured to permit engagement with an artificial airway, such as a tracheostomy tube. A housing member defines an internal chamber in communication with the tracheostomy tube that allows a patient to simultaneously breathe through the tube and adaptor. In one embodiment, a series of projections or ribs extend radially inward within the housing of the adaptor, thereby defining channels which enable the patient's ability to breathe.

The adaptor may contain within the housing an oxygen port for patients having reduced respiratory capacity. As such, the oxygen port permits the introduction of oxygen or oxygen enriched air to the patient.

The adaptor also may contain a means for cleaning mucus and other secretions from the external surface of the catheter. In one embodiment, the housing of the adaptor may have a lavage port to assist in cleaning. A cover may be provided for isolation of the catheter from the atmosphere during cleaning.

Further, the adaptor of the invention, when used with a closed suction catheter assembly, safeguards the clinician from contamination by keeping the external surface of the catheter either within the protective sleeve of the closed suction catheter assembly or within the adaptor housing. The isolation of the catheter further safeguards the patient by keeping microbes and other surrounding contaminants away from the external surface of the catheter.

The adaptor also facilitates release of the closed suction catheter assembly from the tracheostomy tube and, thus, the patient. A release assembly may include an extension mechanism attached to a release member. When force is applied to the release assembly, the distal end of the closed suction catheter assembly disengages itself from the adaptor flange of the tracheostomy tube. The adaptor permits single-handed detachment without undue movement of the tracheostomy tube.

In one embodiment, the adaptor is formed with a release plate and a pair of arms which attach the plate to the closed suction catheter assembly. The arms are formed so that when pressure is applied thereto, the arms extend, causing the release plate to disengage the adaptor flange of the tracheostomy tube, forcing the distal end of the catheter assembly to move away from the proximal end of the tracheostomy tube.

In accordance with another aspect of the present invention, the release plate may be movable so that a portion of the plate covers the distal end of the catheter to help prevent cross-contamination.

In another embodiment, the adaptor may include a filter for patients who require filtered air. The release mechanism and the filter may form an integrated adaptor unit which is detachable from the closed suction catheter assembly and the tracheostomy tube.

In accordance with yet another aspect of the present invention, the release assembly can be integrated with the manifold of a closed suction catheter assembly which is configured for use on a ventilated patient.

DETAILED DESCRIPTION OF PREFERRED EMBODIMENTS

Figure 1:
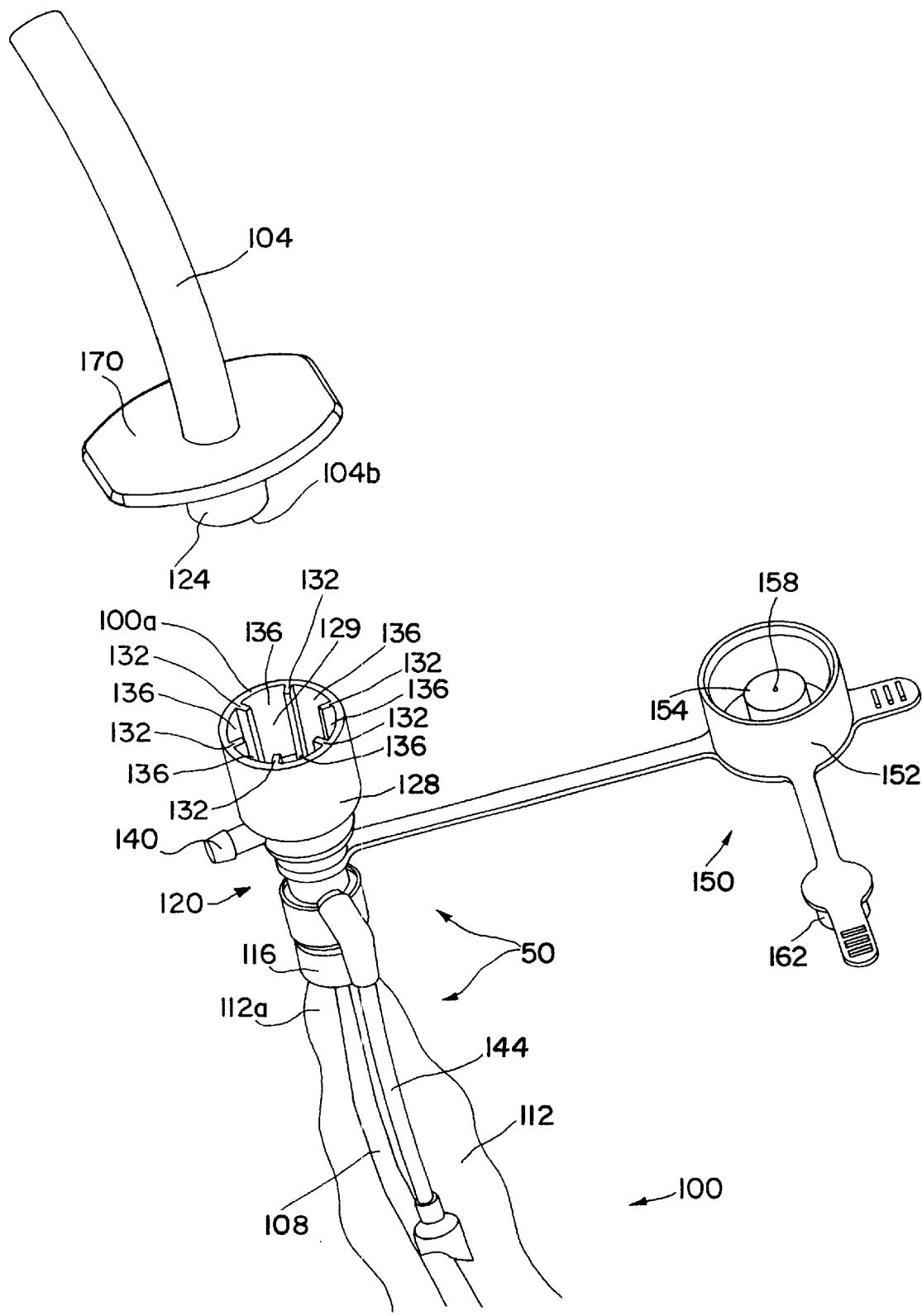
FIG. 1 is a perspective view of a distal end of a closed suction catheter system for attachment to a tracheostomy tube.

Reference will now be made in detail to embodiments of the invention, one or more examples of which are shown in the drawings. It should be appreciated that each example is provided by way of explaining the invention, and not as a limitation of the invention. For example, features illustrated or described with respect to one embodiment may be used with another embodiment to yield still a further embodiment. Such modifications and variations are within the scope and spirit of the invention.

FIG. 1 is a perspective view of a closed suction catheter assembly 100 including a closed suction catheter system 50 having a distal end with the present inventive adaptor 120. The closed suction catheter system 50 is positioned for attachment to an artificial airway, in particular to tracheostomy tube 104. The catheter assembly 100 typically includes an elongate catheter 108 which may be advanced through the distal end 100a of the catheter assembly 100.

The elongate catheter 108 is surrounded or shielded by a flexible envelope 112 which extends substantially along the length of the catheter 108. The envelope 112 is secured at its distal end 112a by a coupling 116 which contains an opening through which the catheter 108 can be advanced and withdrawn. The coupling may include a snap-fit connection between an outer ring and an inner ring.

Disposed distally from the coupling 116 is the adaptor 120 according to the present invention configured to secure the closed suction catheter assembly 100 to an adaptor barrel 124 at the proximal end 104b of the tracheostomy tube 104. The proximal end of the adaptor may be detachable from the catheter assembly or the adaptor may be integral or non-removably fixed to the catheter assembly. In the illustrated embodiment, the adaptor 120 includes a bell-shaped housing 128 which has a distal end configured to engage the exterior of the adaptor barrel 124. The housing 128 defines an internal chamber 129 that is placed in communication with the tracheostomy tube 104. To enable engagement while simultaneously allowing the patient to breathe through the adaptor 120, a series of projections or ribs 132 extend radially inward from the housing 128 to engage the adaptor barrel 124. A plurality of channels 136 are formed between the ribs 132 to enable inhalation and exhalation through the housing 128.

The housing 128 can also have an oxygen port 140 formed therein through which oxygen enriched air can be supplied to the patient. This is particularly important for a patient with compromised respiratory capacity having an indwelling tracheostomy tube. The housing may also have a lavage port 144 which can be used to inject fluids into the tracheostomy tube. The lavage port 144 may also be used to clean the catheter 108.

The closed suction catheter system 50 may also include a cover 150 which engages the housing 128 to substantially isolate the catheter tube 108 from the outside environment. The cover may be attached to the distal end of the closed suction catheter assembly 100 or the proximal end of housing 128. The cover 150 serves various purposes, as discussed in greater detail below.

Immediately after use, it is important to clean the exterior of the catheter 108. If left uncleaned, mucus and other secretions dry on the catheter 108, reducing its effectiveness in future uses. The mucus can also serve as a breeding ground for microbes. The cover 150 assists in cleaning the catheter 108 by providing a restricted airflow into the distal end of the catheter tube. This is accomplished by a cap 152 which includes a wall 154 having a small hole 158 to form a metering valve. The hole 158 allows a small quantity of air to enter as suction is applied through the catheter 108 to restrict airflow into the catheter. It has been found that providing such a restricted airflow helps to improve cleaning of the distal end of the catheter 108.

A secondary cap 162 may be provided to selectively close the valve formed by the wall 154 and the hole 158. The secondary cap 162 essentially isolates the distal end of the catheter 108 from the surrounding environment and potential contaminants coming through the housing 128. This is important, as the closed suction catheter system 50 may be attached and removed from the tracheostomy tube numerous times during use. The cover 150 helps prevent the closed suction catheter system from being contaminated by contact with contaminants in the atmosphere.

In order to use the closed suction catheter system 50 again, the cover 150 is removed and the adaptor housing 128 is reattached to the adaptor barrel 124 of the tracheostomy tube 104. To prevent excess movement of the tracheostomy tube 104, the clinician will typically hold the adaptor flange 170 of the tracheostomy tube 104 as the ribs 132 of the adaptor housing 128 are brought into frictional engagement with the adaptor barrel 124.

Figure 2:
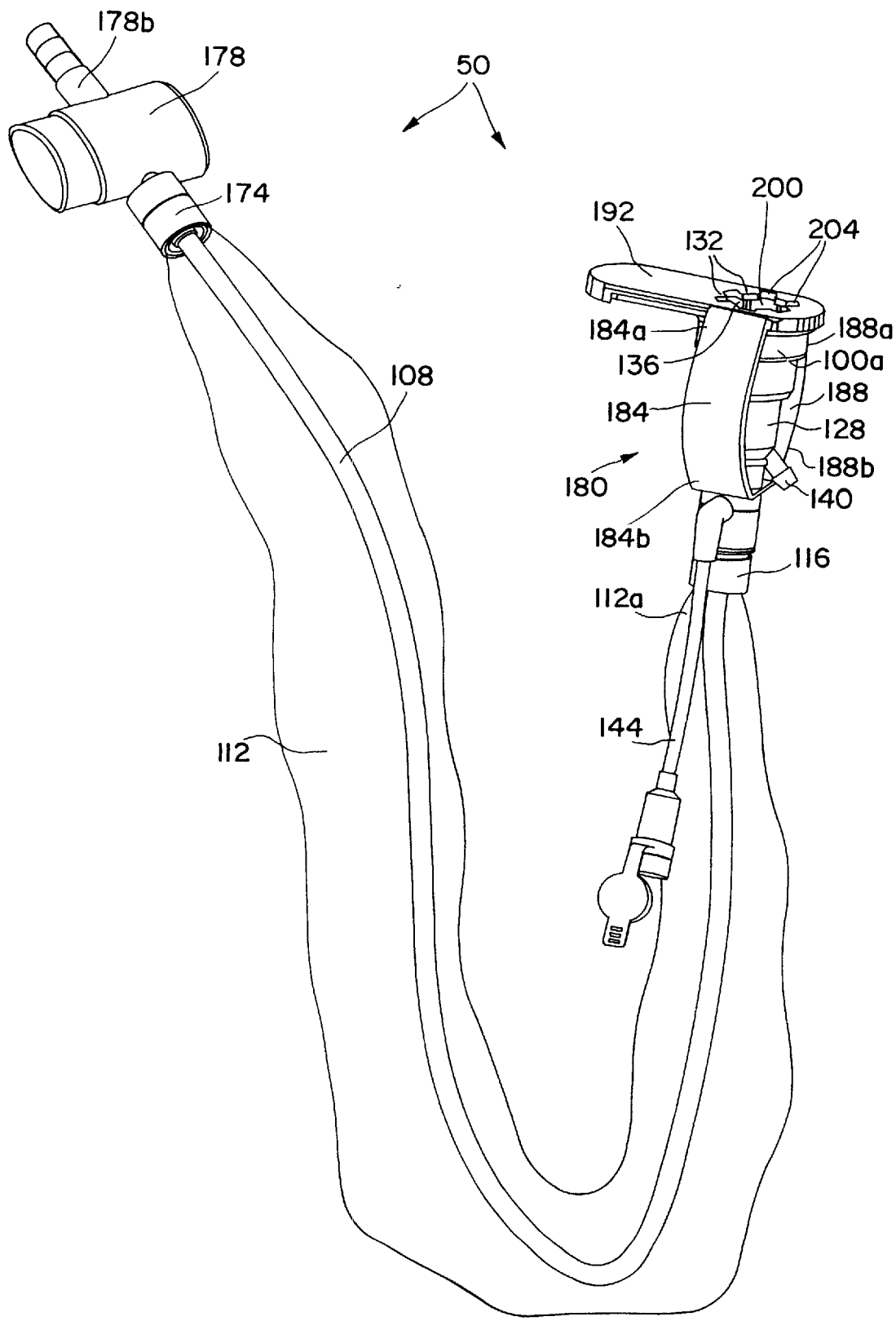
FIG. 2 is a perspective view of a closed suction catheter system having a release adaptor disposed at the distal end of the closed suction catheter assembly in accordance with the principles of the present invention.

FIG. 2 shows the proximal coupling 174 of the envelope 112, and a suction control valve 178 which were not shown in FIG. 1. The suction control valve 178 has a proximal end 178b which connects to a tube attached to a suction source. Referring to FIG. 2, the adaptor also includes a release assembly 180 which is attached to the adaptor housing 128. The release assembly 180 includes a first arm 184 and a second arm 188. A proximal end 184b of the first arm 184 and a proximal end 188b of the second arm 188 are connected to the housing 128. An opposing distal end 184a of the first arm 184 and an opposing distal end 188a of the second arm 188 are attached to an elongate release member 192 having an aperture 200 at one end. The aperture 200 includes a plurality of flutes 204 which are generally in alignment with the channels 136 in the housing 128 to facilitate breathing by the patient.

When the housing 128 is attached to the tracheostomy tube 104, the release member 192 is disposed adjacent to the adaptor flange 170. Applying pressure on the first and second arms 184 and 188 causes the arms to extend distally and to push the release member 192 away from the housing 128 and into engagement with the adaptor flange 170 of the tracheostomy tube 104. Forcible engagement of the release member 192 against the adaptor flange 170 stops the distal movement of the release member and causes a proximal movement of the housing 128. The proximal movement of the housing 128 is sufficient to pull the housing out of engagement with the adaptor barrel 124 of the tracheostomy tube 104. Thus, by squeezing the arms 184 and 188, the clinician can disconnect the housing 128 from the tracheostomy tube 104 without twisting or other forces which tend to move the tracheostomy tube and cause discomfort to the patient.

Figure 3:
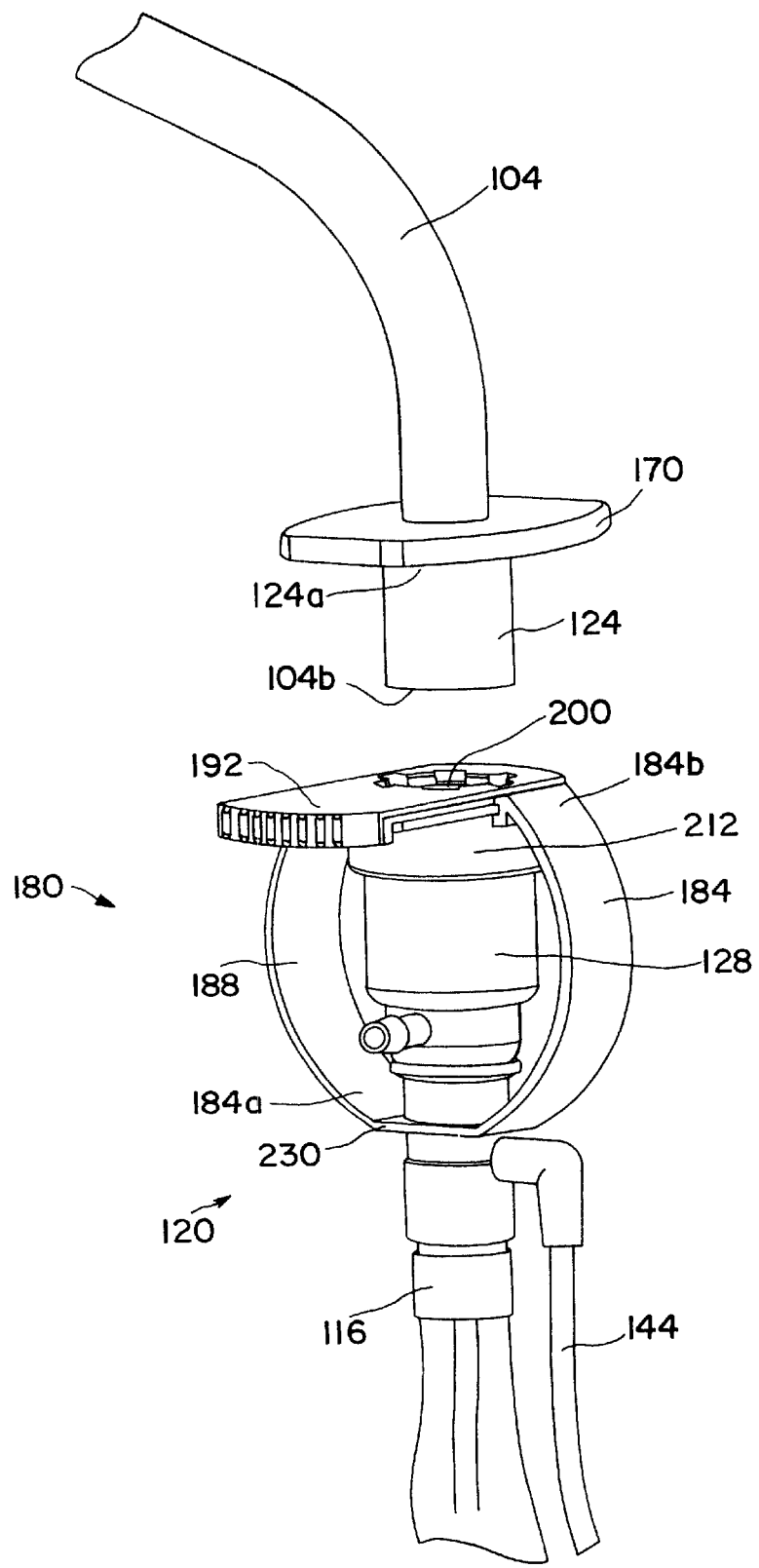
FIG. 3 is a side view of the distal end of the closed suction catheter system of FIG. 2 in alignment for attachment to a tracheostomy tube.

Turning now to FIG. 3, there is shown a side view of the distal end of the adaptor 120. The view more clearly shows the release assembly 180, including the first and second arms 184 and 188 and the release member 192. The first and second arms 184 and 188 may be in a curved, relaxed state so that the release member 192 is disposed adjacent the housing 128. Preferably, a telescoping ring 212 is disposed at the distal end of the housing 128 and is attached to the release member 192 to form an extension to the housing when the arms 184 and 188 are compressed and the release member 192 is moved away from the housing.

Figure 4:
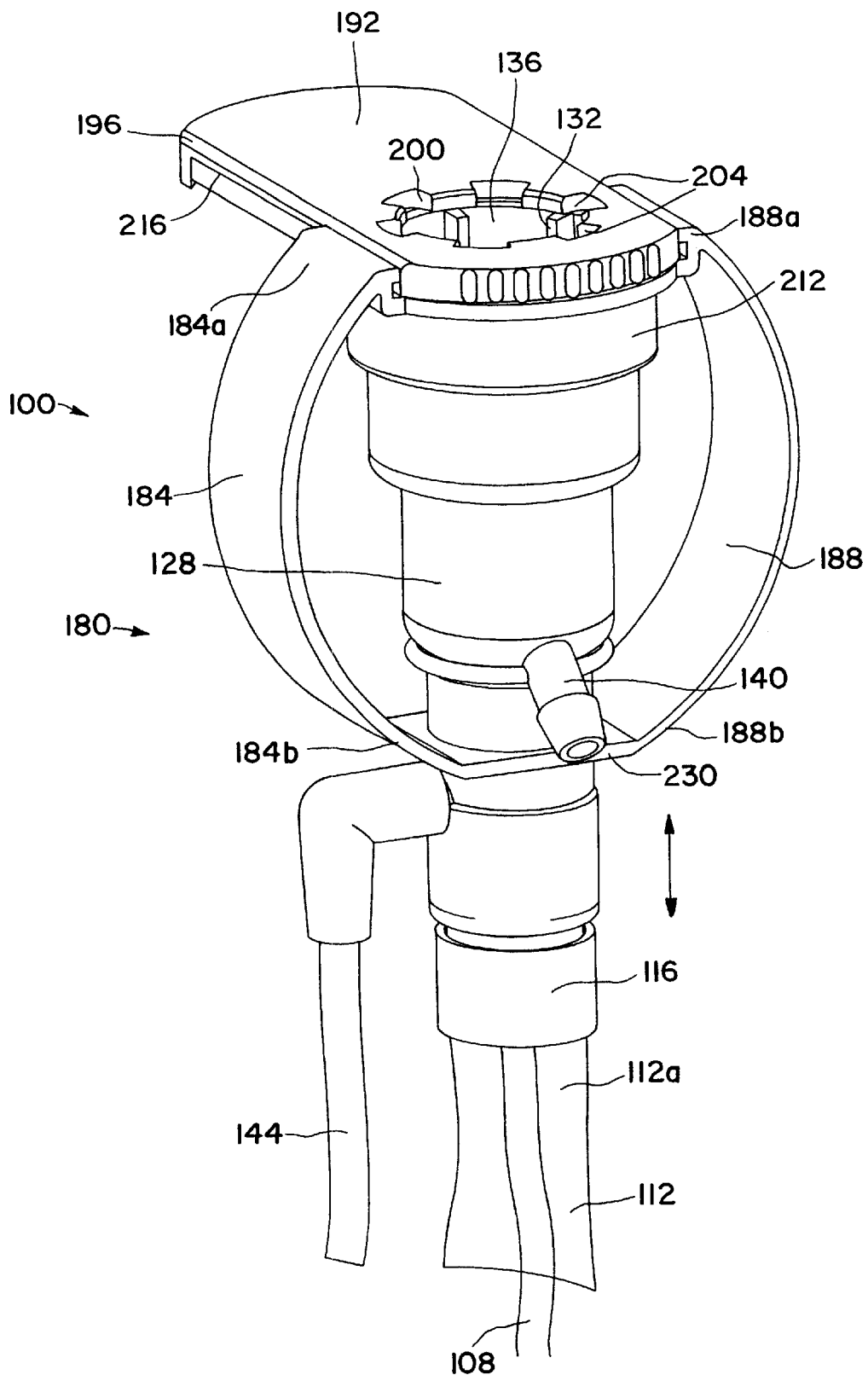
FIG. 4 is a close-up perspective view of the closed suction catheter system of FIGS. 2 and 3 with the release adaptor configured for attachment to a tracheostomy tube.

FIG. 4 illustrates the release assembly 180 in greater detail. The release assembly 180 includes the arms 184 and 188 and the release member 192 in the form of a release plate 196. Plate 196 may also be used as a cover, as explained in greater detail below. As shown in FIG. 4, the release member 192 is oriented so that the proximal end of a tracheostomy tube can be inserted through the aperture 200 and into frictional engagement with the ribs 132 in the housing 128. While the sides of the aperture 200 are formed to provide flutes 204 which correspond with the channels 136 in the housing, the inner extreme of the aperture is preferably not in engagement with the adaptor barrel 124 of the tracheostomy tube during use. It may, however, engage a small flange or similar structure (not visible in the Figure) at the bottom of the adaptor barrel 124 when the arms 184 and 188 have been compressed and the release member forced distally from the housing 128.

Figure 5:
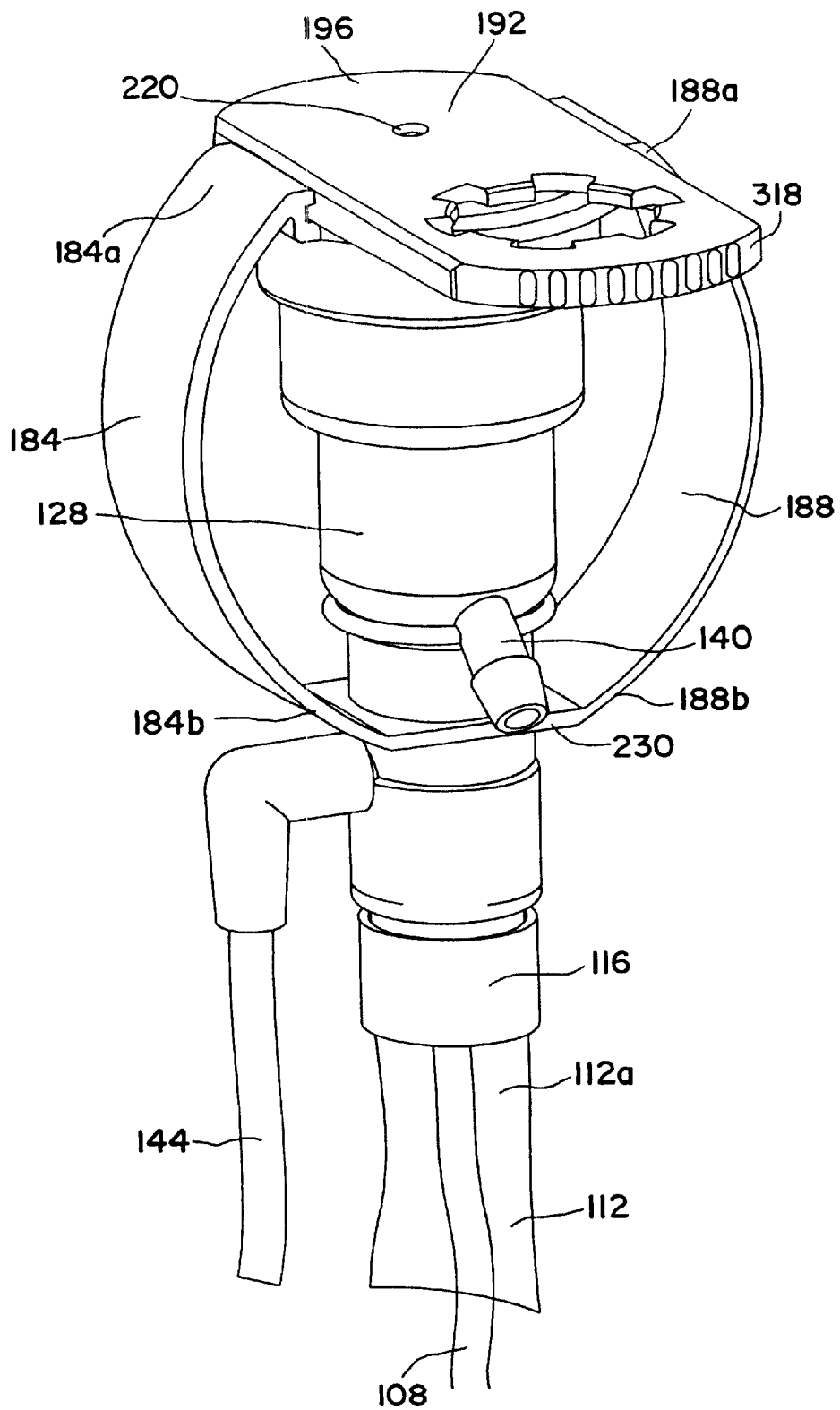
FIG. 5 is a close-up perspective view similar to that of FIG. 4, but with the release adaptor configured to substantially isolate the catheter assembly from contamination while the assembly is not in use.

FIG. 4 also demonstrates a pair of rails 216 (only one of which can be seen) that are disposed on the sides of the release plate 196. The rails 216 are slidably engaged with the distal end 184a of the first arm 184 and the distal end 188a of the second arm 188. When the catheter assembly 100 is not in use, the release member 192 can be slid longitudinally along the rails 216 wherein the plate 196 forms a cover for the distal end of the closed suction catheter system, as shown in FIG. 5. While shown as a solid plate 196 covering the aperture 200, the release member 192 can have a small hole 220 formed therein to facilitate cleaning of the distal end of the catheter 108.

Figure 6:
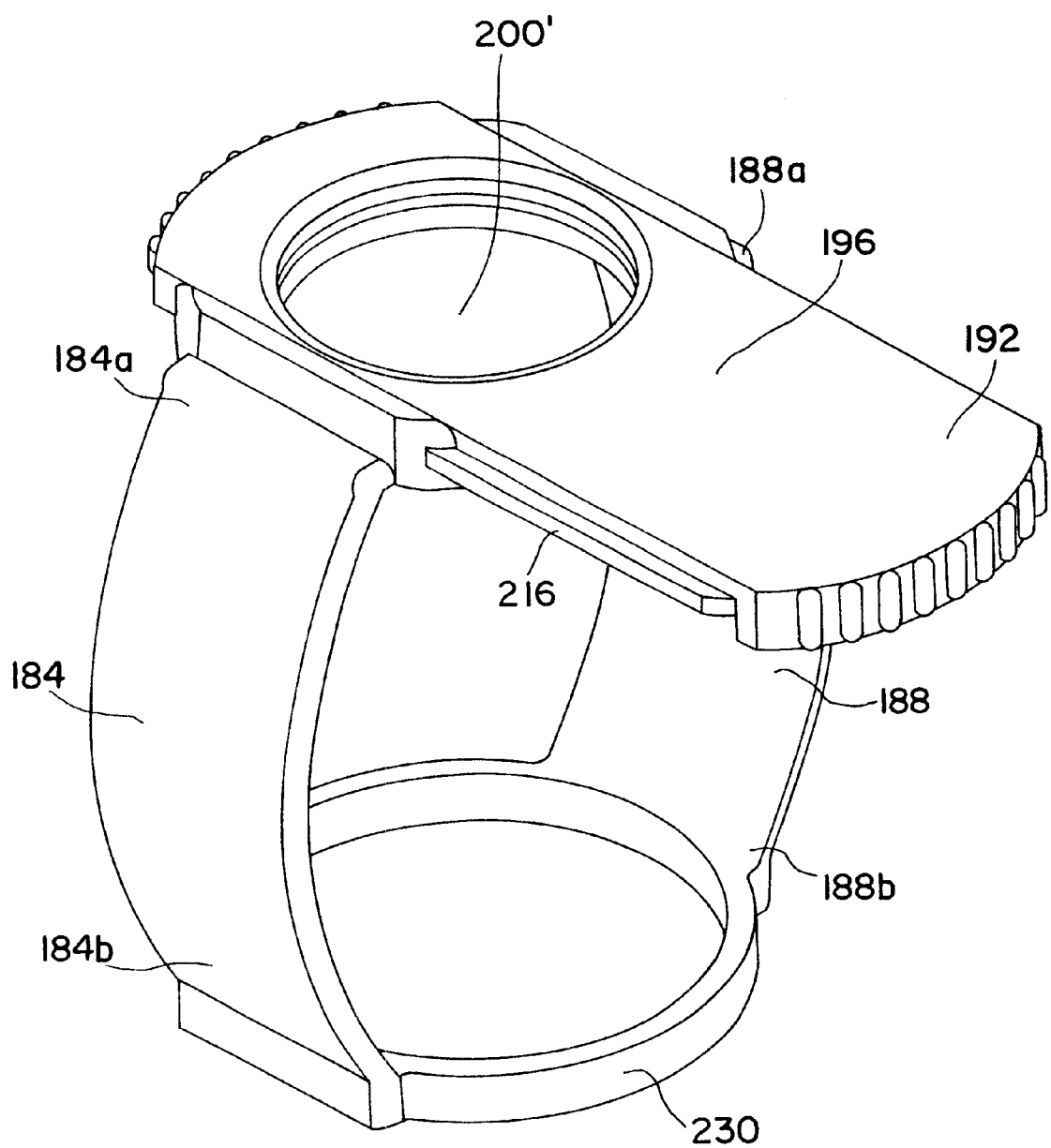
FIG. 6 is a close-up perspective view of a release assembly apart from the adaptor onto which it is typically mounted.

FIG. 6 shows a perspective view of a release assembly which is substantially the same as the release assembly 180 of FIGS. 2 through 4. The two arms 184 and 188, shown in a resting state, are preferably molded to form a single piece of material with a retaining collar 230 disposed therebetween. The retaining collar 230 is configured for mounting on the distal end 100a (FIG. 2) of closed suction catheter assembly 100 on or slightly above the housing 128. The retaining collar 230 preferably remains stationary so that compression of the arms will cause maximal distal extension of the release member 192.

As shown in FIG. 6, the release member 192 is the same as that of FIGS. 2 through 4, with the exception that the aperture 200' is not fluted. If the closed suction catheter system is being used by a patient who needs artificial respiration, the diameter size of the aperture 200' may be made sufficiently large such that air can readily flow into the aperture 200' while keeping the adaptor barrel 124 secured within the housing. If the patient using the assembly needs to breathe through a filter, the diameter of aperture 200' need only be slightly larger than the adaptor barrel 124 (FIG. 3) of the tracheostomy tube 104 (FIG. 3).

Figure 7:
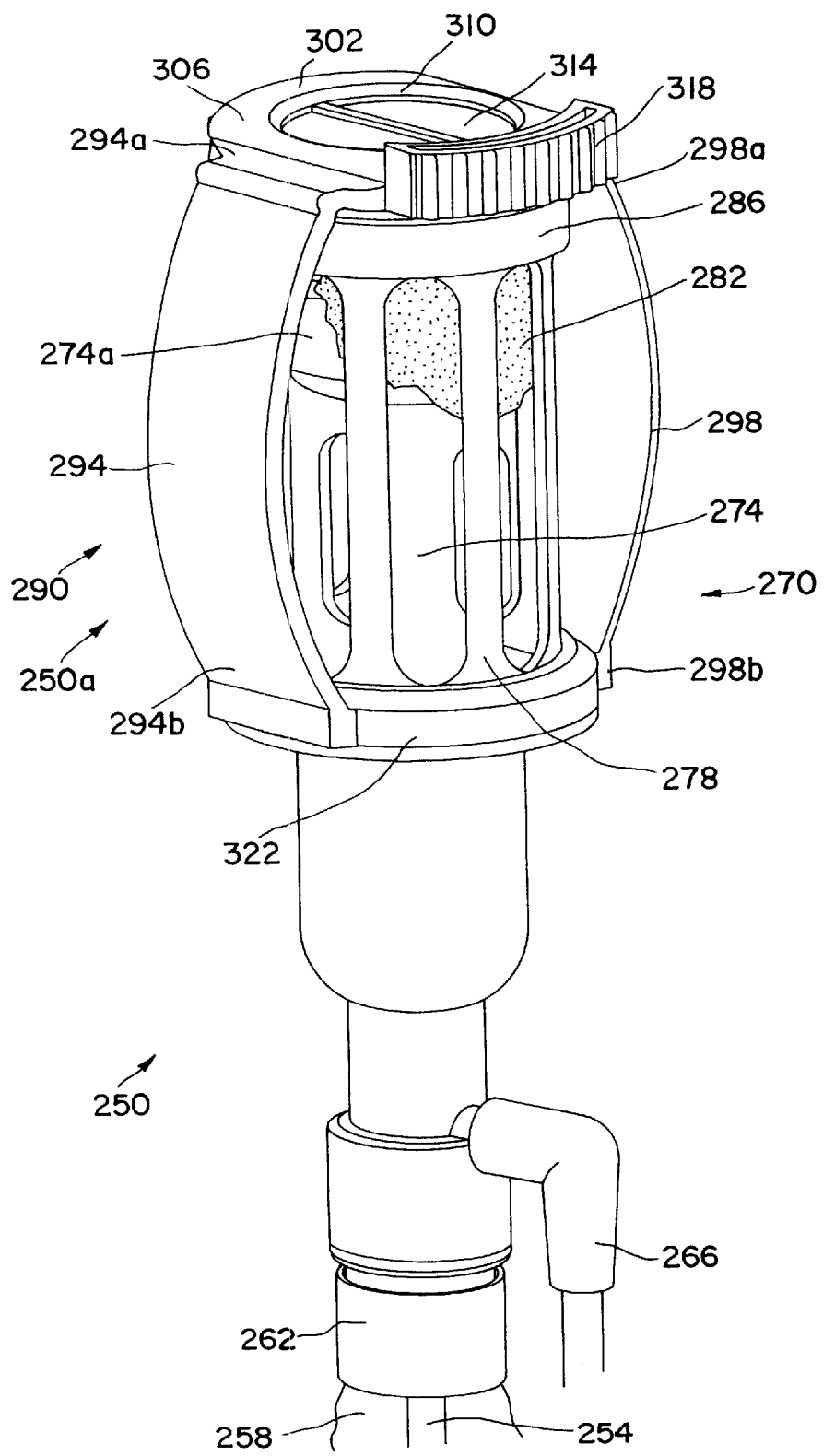
FIG. 7 is a close-up perspective view of an alternate embodiment of the invention wherein a filter is integrated into an adaptor with a release mechanism.

FIG. 7 shows a close-up view of a distal end 250a of a closed suction catheter system 250 with an alternate embodiment of the invention. The closed suction catheter system 250 includes a catheter 254 which is enclosed within an envelope 258. As with the prior embodiment, the envelope 258 is secured at its distal end by a coupling 262 which allows the catheter 254 to be advanced therethrough. A lavage port 266 may also be provided for injecting liquids and/or washing the catheter 254 after use.

The differences between the embodiment shown in FIG. 7 and that shown in FIGS. 2 through 5 are present in the adaptor, generally indicated at 270. The adaptor housing 274 is formed, in part, by a filter housing 278. A filter material 282 is disposed in the filter housing 278 to enable respiration of a patient through the filter material. The filter material may be selected primarily to prevent cross-contamination between the patient and the surrounding environment, or could be selected to serve as a heat and moisture exchanger (HME). While not shown in FIG. 7, an oxygenation port, such as port 140 in FIGS. 1, 2, 4 and 5, may also be provided to enrich the air.

A circular receptor, such as receptor 286, may be provided at either end of housing 274 to frictionally engage the proximal end 104a (FIGS. 1 and 4) of the tracheostomy tube 104. Because the patient is able to breathe through the filter material 282, ribs and channels, such as those discussed with respect to the embodiment of FIGS. 2 through 5 need not be provided.

The adaptor assembly 270 also includes a release assembly, generally indicated at 290. The release assembly 290 includes a first arm 294 and a second arm 298. The distal end 294a of the first arm 294 and the distal end 298a of the second arm 298 are attached to a release member 302 in the form of an annular disk 306 surrounding an aperture 310. The aperture 310 may be selectively closed by a sliding cover 314 with a handle 318 formed at one end. The opposing, proximal ends 294b and 298b of the arms 294 and 298 are attached to a retaining ring 322 mounted on the closed suction catheter system 250. Alternatively, the retaining ring 322, the arms 294 and 298, and the release member 302 can be formed as a single part.

Thus, as shown in FIG. 7, the catheter 254 is protected from direct contact with the environment, either by travel of contaminants to the catheter, or by accidental advancement of the catheter beyond the distal end 250a of the closed suction catheter system 250. In order to place the closed suction catheter system 250 into condition for use, the handle 318 would be retracted from the release member 302 to open the aperture.

The release assembly 290 functions in substantially the same manner as the release assembly 180 of FIGS. 2 through 5. Lateral compression of the arms 294 and 298 causes them to distally extend with release member 302. The release member 302 engages the flange 170 of the tracheostomy tube 104 and forces the housing 274 to disconnect from the tracheostomy tube.

Figure 8:
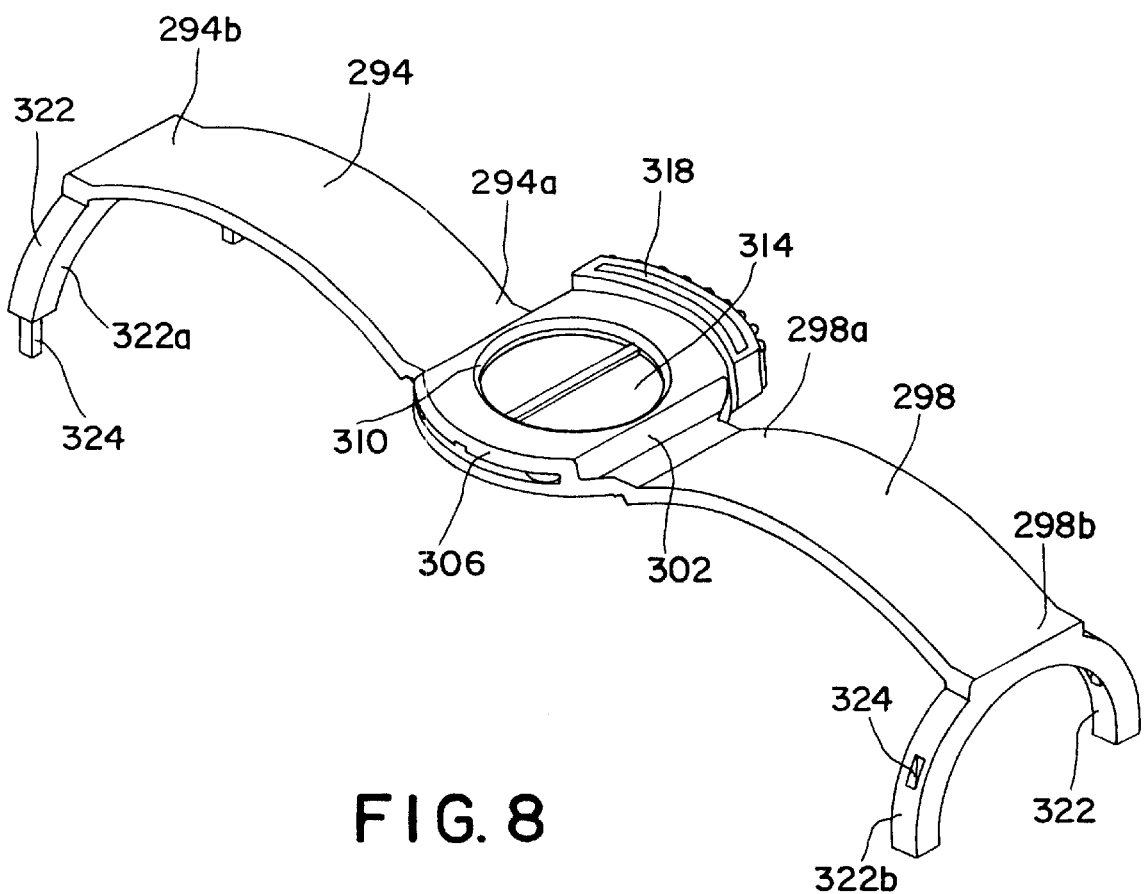
FIG. 8 is a close-up perspective view of the partially disassembled release assembly of FIG. 7 demonstrating an alternative method of assembling the release mechanism.

Turning briefly to FIG. 8, there is shown a close-up view of one embodiment of the release assembly shown in FIG. 7. The release assembly includes the first arm 294, the second arm 298 and the release member 302 formed by the annular disk 306 and aperture 310. The cover 314 is depicted in the closed position. The retaining ring 322 which is opposite the release member 302 is formed of two parts 322a and 322b corresponding to male and female components, respectively, which allow the retaining ring 322 to be snap fitted onto the distal end 250a (FIG. 7) of the closed suction catheter system 250.

Figure 9:
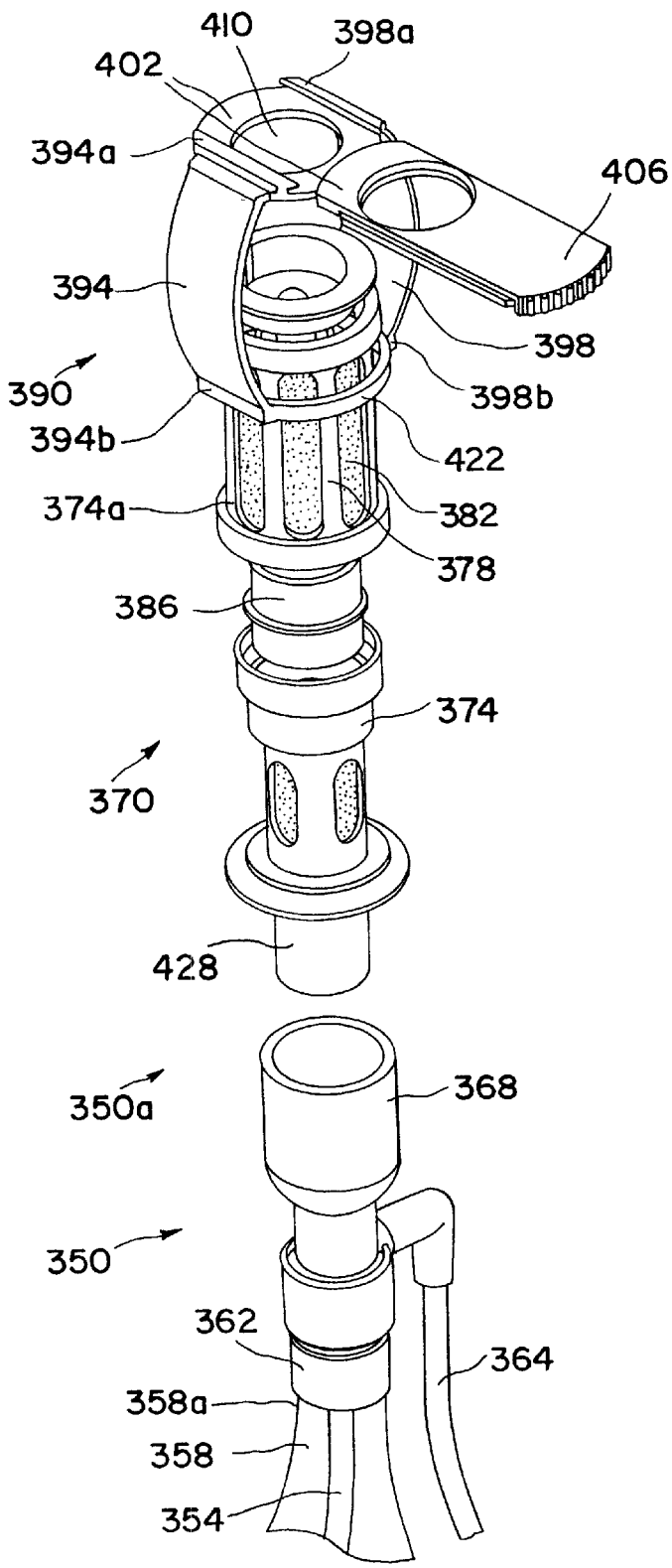
FIG. 9 is a close-up perspective view of yet another embodiment wherein the filter and the release mechanism are formed in an adaptor which is detachable from the remainder of the closed suction catheter system.

Turning now to FIG. 9, there is shown a component view of the distal end 350a of a catheter assembly, generally indicated at 350. The catheter assembly 350 has a catheter 354 and an envelope 358 which is held at its distal end 358a by a coupling 362. A lavage port 364 is also provided distally of the coupling, but proximal to an adaptor 368.

Also disclosed in FIG. 9 is an adaptor assembly, generally indicated at 370, which is attachable to, but releasable from the adaptor 368. The adaptor assembly 370 includes an adaptor housing 374. A filter housing 378 is received in the adaptor housing 374 and has filter material 382 disposed therein to enable respiration of a patient through the filter material. The filter material may be selected primarily to prevent inhalation and exhalation of microbes or to serve as a heat and moisture exchanger (HME). While not shown in FIG. 9, an oxygenation port, such as port 140 in FIGS. 1, 2, 4 and 5, can also be provided to enrich the air.

A solid annular ring 386 is provided for engaging the proximal end (FIGS. 1 and 3) of the tracheostomy tube 104. The annular ring 386 of the housing 374 forms a frictional engagement with the tracheostomy tube until the release assembly, generally indicated at 390, is used to disconnect the two.

The release assembly 390 includes a first arm 394 and a second arm 398. The distal end 394a of the first arm 394 and the distal end 398a of the second arm 398 are attached to a release member 402. The release member 402 has an aperture 410 formed therein. A slide plate 406 is provided to cover and undercover the aperture 410.

The opposing, proximal ends 394b and 398b of the arms 394 and 398 are attached to a retaining ring 422 mounted on the adaptor assembly 370. When assembled, an annular projection 428 extends above the retaining ring 422 to engage the adaptor 368 and thereby hold the adaptor assembly 370 to the adaptor at the distal end 350a of the catheter assembly 350.

While the embodiments of FIGS. 2 through 9 show the use of plates, disks, etc., with an aperture formed therein, those skilled in the art will appreciate that the release member does not need to completely circumscribe the adaptor barrel 124 (FIGS. 1 and 4) of the tracheostomy tube 104. Thus, a release member which is U-shaped or which has a plurality of spaced segments could also be used. Furthermore, the release assembly need not have two arms.

Figure 10:
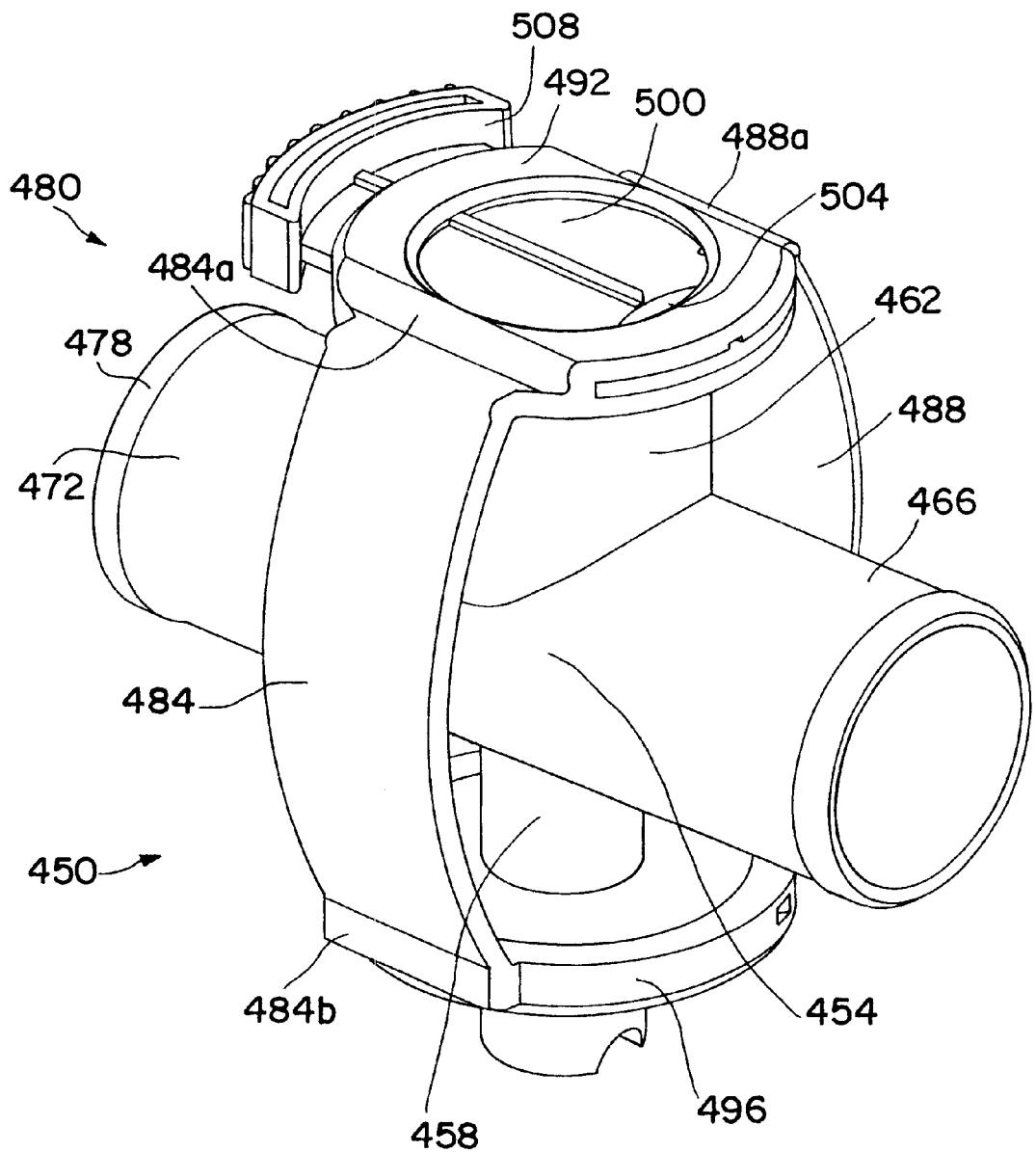
FIG. 10 is a perspective view of an adaptor for use with a closed suction catheter assembly which is used on patients requiring mechanical ventilation.

Turning now to FIG. 10, there is shown another adaptor assembly in accordance with the present invention. The previous embodiments have been taught for use in a context in which the patient may be able to breathe on his or her own. FIG. 10, however, shows a close-up perspective view of an adaptor, generally indicated at 450, which would be disposed at the distal end of a closed suction catheter assembly for use when a patient is mechanically ventilated. The adaptor assembly 450 includes a housing 454 which amp forms a manifold for a patient attached to a mechanical ventilator. The housing 454 has a first barrel 458 disposed at the proximal end of the housing which is configured for advancement of a catheter therethrough. An opposing second barrel 462 is in axial alignment with the first barrel and is configured for attachment to the adaptor barrel 124 (FIGS. 1 and 4) of a tracheostomy tube 104.

A third barrel 466 extends orthogonally from the first and second barrels 458 and 462. The third barrel 466 will generally be attached to a Y-adaptor (not shown) which, in turn, is attached to the inspiratory and expiratory tubing of a mechanical ventilator. In use, air comes from the mechanical ventilator, through the third barrel 466 and through the first barrel 462 into a tracheostomy tube. Exhausted air travels out through the first barrel 462 and then the third barrel 466.

A fourth barrel 472 may also be provided. The fourth barrel 472 is normally covered with a cap (not shown) which fits over a lip 478 on the fourth barrel when the patient is being mechanically ventilated. The cap can be removed however, to provide enriched air through the adaptor, while not forcing ventilation. This procedure is typically referred to as "blow-by" and is often used to wean patients from the ventilator.

The adaptor assembly 450 is also provided with a release assembly, generally indicated at 480. The release assembly 480 includes a first arm 484 and a second arm 488. The first arm 484 is attached to a release member 492 at a distal end 484a and to a retaining ring 496 at an opposing proximal end 484b. Likewise, the second arm 488 is attached to the release member 492 at the distal end 488a and to the retaining ring 496 at the proximal end.

A cover 500 is moveable within the release member 492 to close the aperture 504 and cover the catheter disposed in the manifold. The cover 500 can be moved from the closed position shown in FIG. 10 to an open position simply by pulling the handle 508 away from the aperture 504.

Figure 11:
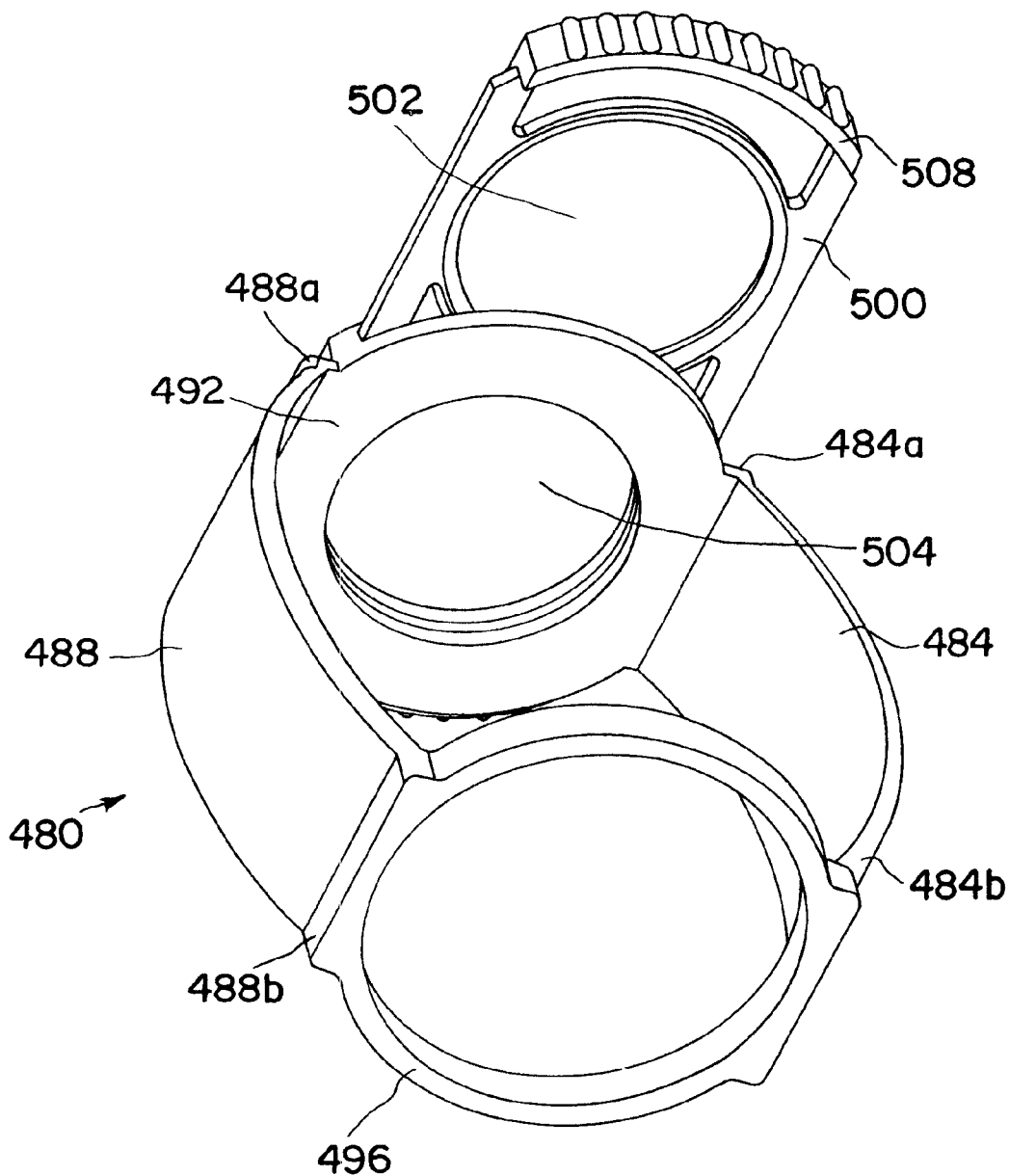
FIG. 11 is a perspective view of the release assembly of FIG. 10 taken from the proximal end of the assembly.

FIG. 11 shows the backside of the release assembly 480 of FIG. 10 with a different cover. The release assembly 480 includes a first arm 484 and a second arm 488. The first arm 484 is attached to the release member 492 at the distal end 484a and to the retaining ring 496 at the opposing proximal end 484b. Likewise, the second arm 488 is attached to the release member 492 at the distal end 488a and to the retaining ring 496 at the proximal end 488b.

The cover 500 is moveable within the release member 492 to close the aperture 504 and cover the catheter disposed in the manifold. The cover 500 can be moved from the closed to open position simply by pulling the handle 508 away from the aperture 504. A recess 502 may be formed in the cover 500 to engage the interior of the release member and hold the cover in a closed position until affirmatively acted on by the clinician. This prevents sliding of the cover 500 and accidental opening.

Figure 12:
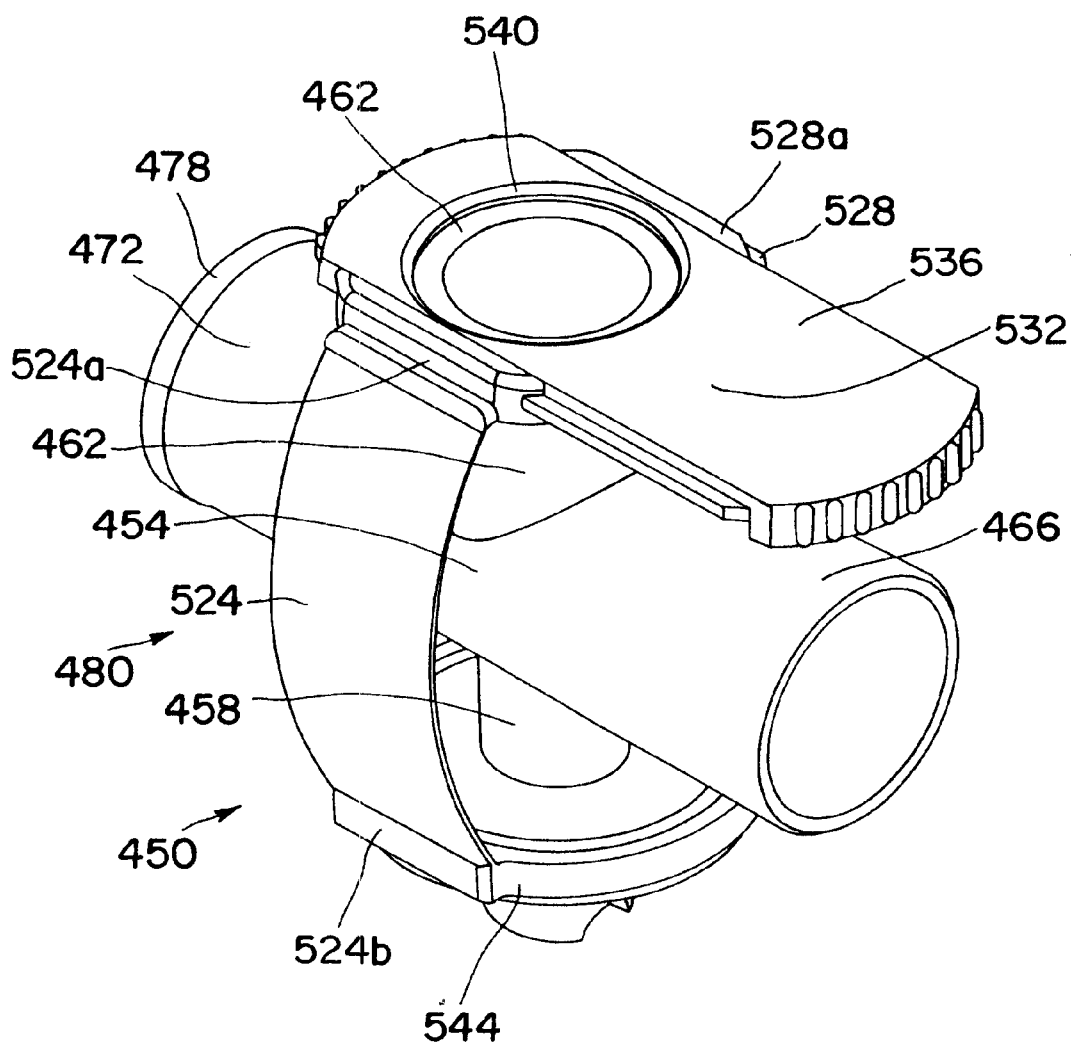
FIG. 12 is a perspective view of another embodiment of an adaptor for use on patients who are receiving mechanical ventilation.

FIG. 12 shows an adaptor assembly, which is substantially identical to the adaptor discussed with respect to FIG. 10 and is numbered accordingly. The adaptor assembly 450 also includes a release assembly which includes first and second arms 524 and 528. The distal end 524a and 528a of each arm is slidably attached to the release member 532 in the form of a release plate 536. The release plate 536 defines an aperture 540 which is moveable into alignment with the second barrel 462. The proximal end 524b of the first arm 524 and the proximal end (not shown) of the second arm 528 are attached to the retaining ring 544. Compressing the arms 524 and 528 causes the release member 532 to extend distally and detach the second barrel 462 from the tracheostomy tube.

Those skilled in the art will appreciate that variations and modifications can be made in the present invention as come within the scope and spirit of the invention.

What is claimed is:

1. An adaptor for connecting a closed suction catheter system to an artificial airway tube, said adaptor comprising a housing defining an internal chamber and having a distal end configured to detachably engage a proximal end of said artificial airway tube, and a proximal end configured for communication with a distal end of said closed suction catheter system; said housing further comprising radially inwardly directed internal structure defining an air access between said housing and the artificial airway tube for air to be inhaled and exhaled by a patient breathing through an artificial airway having said adaptor attached thereto.

2. The adaptor according to claim 1, wherein said internal structure comprises a plurality of radially extending ribs disposed circumferentially around said distal end of said adaptor, said ribs defining air channels therebetween.

3. The adaptor according to claim 1, wherein said housing further comprises an oxygen port.

4. The adaptor according to claim 1, further comprising a release assembly configured with said housing, upon actuation thereof said release assembly separating said housing from said artificial airway tube.

5. The adaptor according to claim 1, wherein said proximal end of said housing is detachably engageable with said closed suction catheter system.

6. The adaptor according to claim 1, wherein said proximal end of said housing is non-removably fixed to said closed suction catheter system.

7. An adaptor for connecting a closed suction catheter system to an artificial airway tube, said adaptor comprising a housing defining an internal chamber and having a distal end configured to detachably engage a proximal end of said artificial airway tube, and a proximal end configured for communication with a distal end of said closed suction catheter system; said housing further comprising internal structure defining an air access for air to be inhaled and exhaled by a patient breathing through an artificial airway having said adaptor attached thereto;

said adaptor further comprising a release assembly configured with said housing, upon actuation thereof said release assembly separating said housing from said artificial airway tube; and wherein said release assembly comprises a slidable release plate having an aperture formed therein and wherein said release plate is slidable to move said aperture into and out of alignment with said internal chamber of said housing.

8. An adaptor for connecting a closed suction catheter system to an artificial airway tube, said adaptor comprising a housing defining an internal chamber and having a distal end configured to detachably engage a proximal end of said artificial airway tube, and a proximal end configured for communication with a distal end of said closed suction catheter system; said housing further comprising internal structure defining an air access for air to be inhaled and exhaled by a patient breathing through an artificial airway having said adaptor attached thereto;

said adaptor further comprising a release assembly configured with said housing, upon actuation thereof said release assembly separating said housing from said artificial airway tube; and wherein said release assembly comprises at least one resilient and compressible arm member, said arm member anchored at one end thereof relative to said housing.

9. The adaptor according to claim 8, wherein said release assembly comprises oppositely disposed first and second said arm members secured to said housing by a retaining ring.

10. An adaptor for connecting a closed suction catheter system to an artificial airway tube, said adaptor comprising a housing defining an internal chamber and having a distal end configured to detachably engage a proximal end of said artificial airway tube, and a proximal end configured for communication with a distal end of said closed suction catheter system; said housing further comprising internal structure defining an air access for air to be inhaled and exhaled by a patient breathing through an artificial airway having said adaptor attached thereto;

said adaptor further comprising a release assembly configured with said housing, upon actuation thereof said release assembly separating said housing from said artificial airway tube; and wherein the release assembly comprises a release member disposed at said distal end of said adaptor, said release member movable distally upon actuation of said release assembly to disengage said housing from said artificial airway tube.

11. The adaptor according to claim 10, further comprising at least one resilient and compressible arm member attached at one end thereof to said release member and anchored at an opposite end thereof to said housing, whereupon compression of said arm member causes said release member to move distally relative to said housing.

12. An adaptor for connecting a closed suction catheter system to an artificial airway, said adaptor comprising:
   a housing defining an internal chamber and having a distal end configured to detachably engage a proximal end of said artificial airway tube, and a proximal end configured for communication with a distal end of said closed suction catheter assembly; and
   a release assembly configured on said housing to separate said housing from the artificial airway upon actuation of said release assembly.

13. An adaptor for connecting a closed suction catheter system to an artificial airway, said adaptor comprising:
   a housing defining an internal chamber and having a distal end configured to detachably engage a proximal end of said artificial airway tube, and a proximal end configured for communication with a distal end of said closed suction catheter assembly;
   a release assembly configured on said housing to separate said housing from the artificial airway upon actuation of said release assembly; and
   wherein said release assembly comprises a slidable release plate having an aperture formed therein and wherein said release plate is slidable to move said aperture into and out of alignment with said internal chamber of said housing.

14. An adaptor for connecting a closed suction catheter system to an artificial airway, said adaptor comprising:
   a housing defining an internal chamber and having a distal end configured to detachably engage a proximal end of said artificial airway tube, and a proximal end configured for communication with a distal end of said closed suction catheter assembly;
   a release assembly configured on said housing to separate said housing from the artificial airway upon actuation of said release assembly; and
   wherein said release assembly comprises at least one resilient and compressible arm member, said arm member anchored at one end thereof relative to said housing.

15. The adaptor according to claim 14, wherein said release assembly comprises oppositely disposed first and second said arm members secured to said housing by a retaining ring.

16. An adaptor for connecting a closed suction catheter system to an artificial airway, said adaptor comprising:
   a housing defining an internal chamber and having a distal end configured to detachably engage a proximal end of said artificial airway tube, and a proximal end configured for communication with a distal end of said closed suction catheter assembly;
   a release assembly configured on said housing to separate said housing from the artificial airway upon actuation of said release assembly; and
   wherein said release assembly comprises a release member disposed at said distal end of said adaptor, said release member movable distally upon actuation of said release assembly to disengage said housing from said artificial airway tube.

17. The adaptor according to claim 16, wherein said release assembly consists of a release member disposed at the distal end of the adaptor and which may be extended distally to disengage the housing from the artificial airway tube.

18. An adaptor for connecting a closed suction catheter system to an artificial airway, said adaptor comprising:
   a housing defining an internal chamber and having a distal end configured to detachably engage a proximal end of said artificial airway tube, and a proximal end configured for communication with a distal end of said closed suction catheter assembly;
   a release assembly configured on said housing to separate said housing from the artificial airway upon actuation of said release assembly; and
   wherein said adaptor housing includes a manifold having a first barrel, a second barrel, and a third barrel, said first and second barrels being substantially in alignment and said third barrel extending perpendicularly thereto.

19. The adaptor according to claim 18, wherein said manifold further contains a fourth barrel.

20. An adaptor for connecting a closed suction catheter system to an artificial airway, said adaptor comprising:
   a housing defining an internal chamber and having a distal end configured to detachably engage a proximal end of said artificial airway tube, and a proximal end configured for communication with a distal end of said closed suction catheter assembly;
   a release assembly configured on said housing to separate said housing from the artificial airway upon actuation of said release assembly; and
   wherein said housing further contains a filter housing and filter material disposed within said filter housing.

21. A catheter system comprising:
   a closed suction catheter assembly;
   an adaptor for connecting said closed suction catheter system to an artificial airway tube, said adaptor comprising a housing defining an internal chamber and having a distal end configured to detachably engage a proximal end of said artificial airway tube, and a proximal end in communication with a distal end of said closed suction catheter assembly; said housing further comprising radially inwardly directed internal structure defining an air access between said housing and the artificial airway tube for air to be inhaled and exhaled by a patient breathing through an artificial airway having said adaptor attached thereto.

22. A catheter system comprising:
   a closed suction catheter assembly;
   an adaptor for connecting said closed suction catheter assembly to an artificial airway, said adaptor comprising:
      a housing defining an internal chamber and having a distal end configured to detachably engage a proximal end of an artificial airway tube, and a proximal end configured in communication with a distal end of said closed suction catheter assembly; and
      a release assembly configured on said housing to separate said housing from the artificial airway upon actuation of said release assembly.

23. An apparatus for suctioning secretions from a patient intubated with a tracheostomy tube, said apparatus comprising:

a closed suction catheter assembly having a catheter tube and an envelope surrounding said catheter tube;

an adaptor disposed at a distal end of said closed suction catheter assembly, said adaptor engageable with a proximal end of the tracheostomy tube, said catheter tube advanceable through said adaptor and into the tracheostomy tube; and a cover attached to a distal end of said adaptor, said cover slideably engageable with said adaptor to selectively isolate said adaptor and said closed suction catheter from the atmosphere upon detachment of said adaptor from the tracheostomy tube.

24. An apparatus for suctioning secretions from a patient intubated with a tracheostomy tube, said apparatus comprising:

a closed suction catheter assembly having a catheter tube and an envelope surrounding said catheter tube;

an adaptor disposed at a distal end of said closed suction catheter assembly, said adaptor engageable with a proximal end of the tracheostomy tube, said catheter tube advanceable through said adaptor and into the tracheostomy tube;

a cover attached to a distal end of said adaptor, said cover engageable with said adaptor to selectively isolate said adaptor and said closed suction catheter from the atmosphere upon detachment of said adaptor from the tracheostomy tube; and wherein said cover comprises an end wall having a hole defined therethrough to permit air to be drawn into said catheter assembly upon suction being applied to said catheter tube during cleaning of said catheter tube.

25. The apparatus of claim 24, wherein the cover further comprises a cap to further seal said hole.

26. An apparatus for suctioning secretions from a patient intubated with a tracheostomy tube comprising:

a closed suction catheter assembly having a catheter tube, an envelope and a coupling for holding an end of the envelope; and an adaptor disposed at the distal end of the closed suction catheter assembly and having a housing configured for attachment to an tracheostomy tube and a release assembly disposed adjacent the housing, the release assembly being configured for detaching the housing from the tracheostomy tube responsive to a compressive force to the release assembly.

* * * * *